United States Patent [19]
Broekkamp et al.

[11] Patent Number: 6,150,353
[45] Date of Patent: Nov. 21, 2000

[54] THERAPEUTIC COMBINATIONS OF MIRTAZAPINE AND ANTIPSYCHOTIC AGENTS, FOR THE TREATMENT OR PROPHYLAXIS OF PSYCHOTIC DISORDERS

[75] Inventors: Christophorus Louis Eduard Broekkamp, Oss; Hermanus Henricus Gerardus Berendsen, Geffen; Roger Martin Pinder, Oss, all of Netherlands

[73] Assignee: Akzo Nobel N.V., Arnhem, Netherlands

[21] Appl. No.: 09/380,723

[22] PCT Filed: Mar. 25, 1998

[86] PCT No.: PCT/EP98/01920

§ 371 Date: Sep. 7, 1999

§ 102(e) Date: Sep. 7, 1999

[87] PCT Pub. No.: WO98/43646

PCT Pub. Date: Oct. 8, 1998

[30] Foreign Application Priority Data

Mar. 27, 1997 [EP] European Pat. Off. .............. 97200881

[51] Int. Cl.⁷ ........................ A61K 31/55; A61K 31/505; A61K 31/445
[52] U.S. Cl. .................... 514/214.02; 514/220; 514/258; 514/327
[58] Field of Search .............................. 514/214.02, 220, 514/327, 258

[56] References Cited

FOREIGN PATENT DOCUMENTS 24 10 821  9/1975  Germany .
WO 94 02138  2/1994  WIPO .

OTHER PUBLICATIONS

Berendsen et al., *Psychpharmacology*, 135:3:pp. 284–89, 1998.
Gower et al., Arch. Int. Pharmacodyn. Ther., vol. 291, pp. 185–2011, 1988.
Neal–Beliveau et al., *J. Pharm. Experim. Therap.*, vol. 265:1, pp. 204–217, 1993.
Biological Abstracts, vol. 84, ABstract No. 101722, 1987.
Barbhaiya et al., *J. Clin. Psychopharm.*, vol. 16:1, pp. 26–34, 1996 1987.
Patent Abstracts of Japan, vol. 096, No. 1, JP 07 242669, 1995.
Balant–Gorgia et al., *Therapie*, vol. 51:4, pp. 399–402, 1996.

Primary Examiner—William R. A. Jarvis
Attorney, Agent, or Firm—Mary E. Gormley

[57] ABSTRACT

This application relates to a combination of the antidepressant mirtazapine and an antipsychotic agent such as haloperidol for the treatment of psychotic disorders.

10 Claims, 2 Drawing Sheets

THERAPEUTIC COMBINATIONS OF MIRTAZAPINE AND ANTIPSYCHOTIC AGENTS, FOR THE TREATMENT OR PROPHYLAXIS OF PSYCHOTIC DISORDERS

This application is a 371 of PCT/EA98/01920, filed Mar. 25, 1998.

FIELD OF THE INVENTION

The present invention relates to therapeutic combinations of mirtazapine and an antipsychotic agent, to pharmaceutical compositions containing said combinations and to their use in the treatment or prophylaxis of psychotic disorders.

BACKGROUND OF THE INVENTION

The term antipsychotic agent includes those classical antipsychotics which work via dopamine $D_2$ receptor blockade and which are often referred to as "typical" antipsychotics or neuroleptics, and those new antipsychotics which are referred to as "atypical" antipsychotic agents. This atypicality has been defined in a number of ways, but recently it has been defined as the property of providing equal efficacy to established antipsychotic agents while producing fewer extrapyramidal side effects (Meltzer H. Y. Br. J. Psychiatry, 1996, 168 Suppl. 129:23–31). Examples of such typical and atypical antipsychotics include acepromazine, chlorproethazine, chlorpromazine, cyamemazine fluopromazine, methotrimeprazine, promazine, mesoridazine, pericyazine, piperacetazine, pipothiazine, sulforidazine, thioridazine, acetophenazine, carphenazine, dixyrazine, fluphenazine, perazine, perphenazine, prochlorperazine thiopropazate, thioproperazine, trifluperazine, chlorprothixene, flupenthixol, thiothixene, zuclopenthixol, benperidol, bromperidol, droperidol, fluanisone, haloperidol, melperone, moperone, pipamperone, spiperone, timiperone, trifluperidol, fluspirilene, penfluridol, pimozide, amisulpride, raclopride, remoxipride, sulpiride, sultopride, tiapride, molindone, oxypertine, clozapine, loxapine, risperidone, olanzapine, sertindole, quetiapine and ziprasidone.

SUMMARY OF THE INVENTION

It has now been found that the administration of mirtazapine, which is one of the newest antidepressant agents and has been disclosed in U.S. Pat. No. 4,062,848, in combination with an antipsychotic agent is able to enhance the antipsychotic effect of said antipsychotic.

It is a feature of this invention that the use of such drug combinations will enhance the effect of the antipsychotic agent to be used and therefore allow reduced quantities of an antipsychotic agent to be used and furthermore, therefore allow better management of drug related toxicity and side effects.

Thus according to one aspect, the present invention provides a combination comprising mirtazapine and an antipsychotic agent as herein before described. Preferably the combination includes mirtazapine.

It will be understood that the present invention also includes derivatives of mirtazapine and the antipsychotic agents. Such derivatives include the pharmaceutically acceptable salts thereof. Suitable salts include acid addition salts, for example, hydrochloric, fumaric, maleic, citric or succinic acid, these acids being mentioned only by way of illustration and without implied limitation.

Combinations of mirtazapine and an antipsychotic agent may hereinafter be referred to as combinations according to the invention.

It will be appreciated that the compounds of the combination may be administered simultaneously, either in the same or different pharmaceutical formulation or sequentially. If there is sequential administration, the delay in administering the second active ingredient should not be such as to lose the benefit of the efficacious effect of the combination of the active ingredients.

The present invention further provides combinations according to the invention for use in therapy, more particularly in the treatment or prophylaxis of psychotic disorders such as schizophrenia, mania, hyperactivity, substance abuse, emesis and schizophreniaform disorders.

The present invention further includes a method for the treatment of an animal, for example, a mammal including a human, suffering from or liable to suffer from a psychotic disorder, including any of the aforementioned disorders, which comprises administering an effective amount of a combination according to the invention.

A further feature of the present invention is the method of reducing the amount of antipsychotic agent required to produce an antipsychotic effect in an animal which comprises treating said animal with a therapeutically effective amount of a combination according to the present invention.

The present invention also provides the use of mirtazapine in the manufacture of a medicament for administration simultaneously or sequentially with an antipsychotic agent for the treatment and/or prophylaxis of a psychotic disorder. It will be appreciated that an antipsychotic agent may be used in the manufacture of the above medicament for administration simultaneously or sequentially with mirtazapine.

Administration of an antipsychotic agent in combination with mirtazapine allows a lower dosing of the antipsychotic agent to achieve the same antipsychotic effect. The dosage of the antipsychotic agent may be reduced by 25–90%, for example, 40–80% and typically 50–70%.

The reduction in the amount of antipsychotic agent required will be dependent on the amount of mirtazapine given. Typically the dose of mirtazapine used is that described infra.

Figure 1:
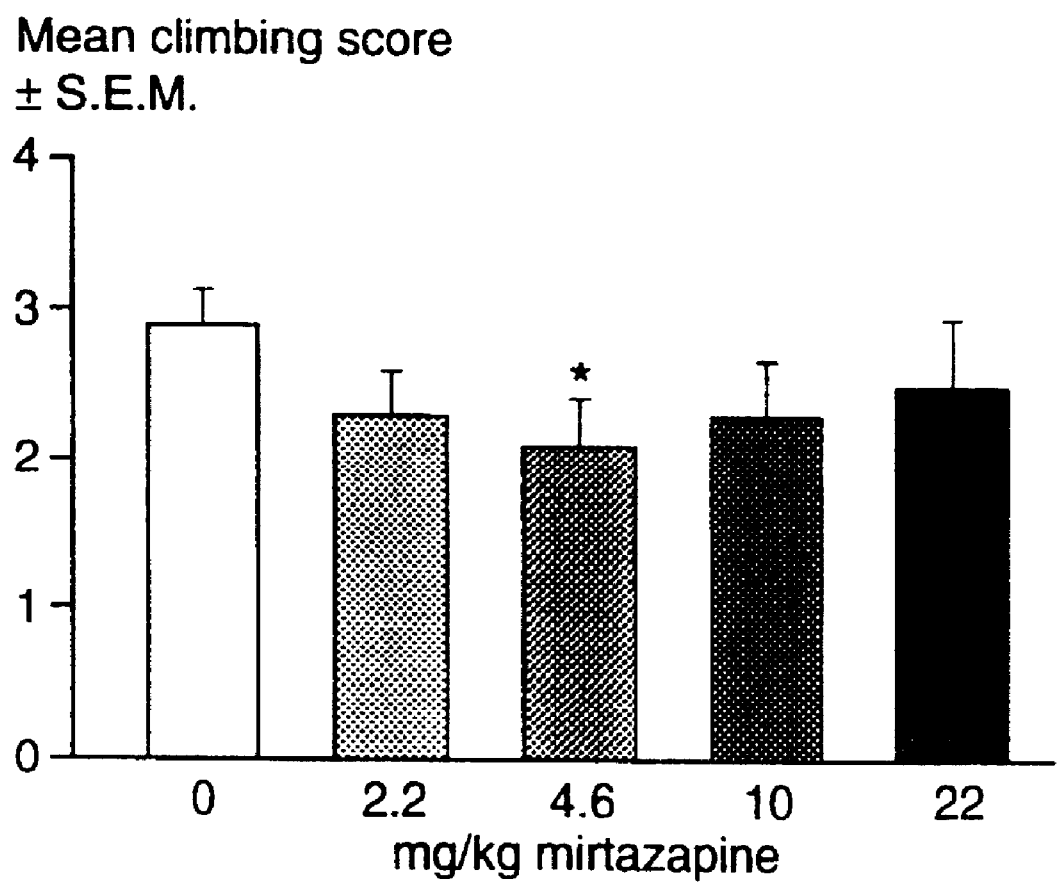
FIG. 1 shows the effect of mirtazapine on apomorphine (1 mg/kg)-induced climbing behaviour in mice. Mirtazapine was injected s.c 30 min before apomorphine. *P<0.05 if compared to placebo treatment.

*P<0.05; P<0.01; *P<0.001 if compared to placebo+ placebo treated group. °P<0.05; °°P<0.01 if compared to placebo+haloperidol treated group.

DETAILED DESCRIPTION OF THE INVENTION

The amount of a combination of mirtazapine and an antipsychotic agent required to produce the efficacious effect will, of course, vary and is ultimately at the discretion of the medical practitioner. The factors to be considered include the route of administration and nature of the formulation, the animal's body weight, age and general condition and the nature and severity of the disease to be treated.

In general, a suitable dose of mirtazapine for administration to a human will be in the range of 0.01 to 30 mg per kilogram body weight of the recipient per day, preferably in the range of 0.1 to 5 mg per kilogram body weight per day and most preferably in the range of 0.3 to 1.0 mg per kilogram body weight per day.

A suitable dose of an antipsychotic agent will be in the range of 0.001 to 25 mg per kilogram body weight of the recipient per day, preferably in the range of 0.1 to 10 mg per kilogram body weight per day and most preferably in the range 0.25 to 5 mg per kilogram body weight per day.

The components of the combination which may be referred to as active ingredients may be administered for therapy to an animal e.g. a mammal including a human in a conventional manner.

While it is possible for the active ingredients of the combination to be administered as the raw chemical it is preferable to present them as a pharmaceutical formulation. Pharmaceutical formulations according to the present invention comprise a combination according to the invention together with one or more pharmaceutically acceptable carriers or excipients and optionally other therapeutic agents. The carrier(s) must be acceptable in the sense of being compatible with the other ingredients of the formula and not deleterious to the recipient thereof. When the individual components of the combination are administered separately they are generally each presented as a pharmaceutical formulation.

A combination of mirtazapine and an antipsychotic agent may conveniently be presented as a pharmaceutical formulation in a unitary dosage form. A convenient unitary dosage formulation contains the active ingredients in amounts of from 0.1 mg to 1 g each for example, 5 mg to 100 mg. Typically unit dosages may, for example, contain 5 to 50 mg, preferably 10 mg of mirtazapine.

More commonly these days pharmaceutical formulations are prescribed to the patient in "patient packs" containing the whole course of treatment in a single package, usually a blister pack. Patient packs have an advantage over traditional prescriptions, where a pharmacist divides a patients supply of a pharmaceutical from a bulk supply, in that the patient always has access to the package insert contained in the patient pack, normally missing in traditional prescriptions. The inclusion of a package insert has been shown to improve patient compliance with the physicians instructions.

It will be understood that the administration of the combination of the invention by means of a single patient pack, or patient packs of each formulation, with a package insert directing the patient to the correct use of the invention is a desirable additional feature of this invention. Suitable dosage units of mirtazapine are for instance, 5 to 50 mg and suitable dosage units containing an antipsychotic agent are 0.1 to 100 mg.

According to a further aspect of the invention, there is provided a patient pack comprising at least one active ingredient of the combination of the invention and an information insert containing directions on the use of the combination of the invention.

According to another aspect the invention provides a double pack comprising in association for separate administration either mirtazapine and an antipsychotic agent.

Formulations include those suitable for oral, rectal, nasal, topical (including transdermal, buccal and sublingual), vaginal or parenteral (including subcutaneous, intramuscular, intravenous and intradermal) administration. The formulations may be prepared by any methods well known in the art of pharmacy, for example, using methods such as those described in Gennaro et al., Remington's Pharmaceutical Sciences (18th ed., Mack Publishing Company, 1990, see especially Part 8: Pharmaceutical Preparations and their Manufacture). Such methods include the step of bringing into association the active ingredient with the carrier which constitutes one or more accessory ingredients. Such accessory ingredients include those conventional in the art, such as, fillers, binders, diluents, disintegrants, lubricants, colorants, flavouring agents and wetting agents.

Formulations suitable for oral administration may be presented as discrete units such as pills, tablets or capsules each containing a predetermined amount of active ingredient; as a powder or granules; as a solution or suspension. The active ingredient may also be present as a bolus or paste, or may be contained within liposomes.

Formulations for rectal administration may be presented as a suppository or enema.

For parenteral administration, suitable formulations include aqueous and non-aqueous sterile injection. The formulations may be presented in unit-dose or multi-dose containers, for example, sealed vials and ampoules, and may be stored in a freeze dried (lyophilised) condition requiring only the addition of the sterile liquid carrier, for example, water prior to use.

Formulations suitable for administration by nasal inhalation include fine dusts or mists which may be generated by means of metered dose pressurised aerosols, nebulisers or insufflators.

The compounds of the combination of the present invention may be obtained in a conventional manner. Mirtazapine may be prepared using the methods described in U.S. Pat. No. 4,062,843.

The antipsychotic agents may be prepared by methods known in the chemical literature. Haloperidol may, for example, be synthesized using the methods described in U.S. Pat. No. 3,438,991.

The following examples are intended for illustration only and are not intended to limit the scope of the invention in any way.

The interaction of mirtazapine with the neuroleptic compound haloperidol was evaluated in the apomorphine climbing test. It was found that the effect of haloperidol on apomorphine-induced climbing behaviour was enhanced by mirtazapine.

Administration of the dopamine agonist apomorphine induces in mice a peculiar motor behaviour consisting mainly in rearing or climbing vertical up the walls of the cage. This behaviour is elicited by stimulation of dopamine receptors in the striatum because it is suppressed after coagulation of this structure and facilitated when the receptors in this area are made hypersensitive by pretreatments with 6-hydroxydopamine or haloperidol. Lesions of the nucleus accumbens did not change the climbing behaviour This climbing behaviour induced by apomorphine is antagonised by antipsychotics including clozapine and sulpiride (Protais et al 1976; Costentin et al, 1975, Von Voigtlander et al 1975; Puech et al, 1978; Costall et al 1978).

It is now reported how the inhibition of apomorphine-induced climbing behaviour by haloperidol is influenced by concomitant treatment with the new antidepressant mirtazapine.

Materials and Methods

The test method used is described in Protais et al 1976, Climbing behaviour induced by apomorphine in mice: a simple test for the study of dopamine receptors in striatum. Psychopharmacology 50: 1–6. Male mice (CrL:CD-1(IcR) BR from Charles River, Germany or MFI from Harlan OLAC UK) weighing 21–25 g were used. Groups of 10 mice each were subcutaneously (s.c.) injected with placebo or mirtazapine and a dose of haloperidol or risperidone at the same time. Thirty minutes later all mice were s.c. injected with apomorphine 1 mg/kg or 0.75 mg/kg. Immediately after the apomorphine injection they were placed individually in a wire mesh cylinder (diameter 12 cm, height 14 cm). At 10 and 20 min hereafter the climbing behaviour of the mice is scored as follows: 4 paws on the floor=0; 1 or 2 paws holding the wall=1; 3 or 4 paws holding the wall=2. For each mouse the total score of the observations at 10 and 20 min is calculated and the mean score for each treatment group is determined. The mean score of the control group should be at least 2.0 (maximum possible score is 4.0). An indication of significance is tested with the 2-tailed Yates test.

Results and Discussion

Figure 2:
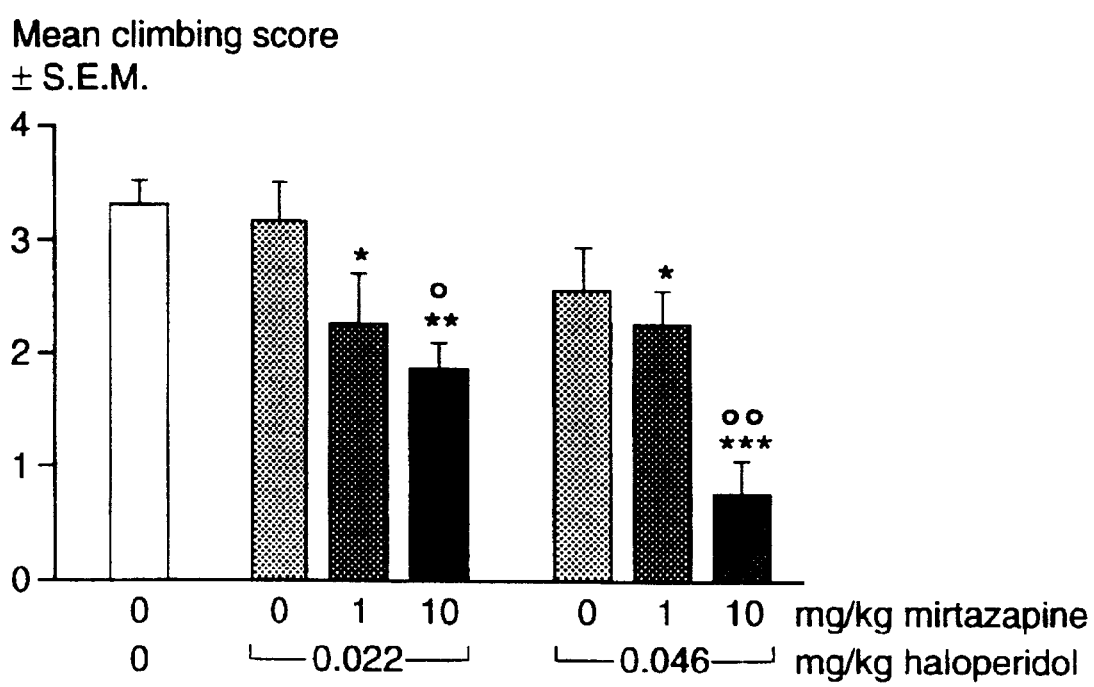
FIG. 2 shows the effect of haloperidol and of haloperidol +mirtazapine treatment on apomorphine (1 mg/kg)-induced climbing behaviour in mice.

The results for the haloperidol experiment are shown in FIG. 1/2. The mean score of the placebo group±standard error of the mean (S.E.M.) was 3.35±0.20. The mean scores±S.E.M. after haloperidol 22 and 46 µg/kg were 3.2±0.33 and 2.6±0.37 respectively. The inhibition of climbing behaviour by haloperidol was dose dependently enhanced if the mice were concomitantly treated with mirtazapine (1 and 10 mg/kg). Results of an experiment with mirtazapine only demonstrated that mirtazapine up to 22 mg/kg had no effect on apomorphine climbing behaviour; see FIG. 2/2.

Results for experiments with risperidone and quetiapine are presented in Tables 1 and 2.

TABLE 1

The figures represent the % inhibition in apomorphine climbing.

| Dose of Risperidone (mg/kg) | A Risp | B Risp + 1 mg Mirt. | C Risp + 10 mg Mirt |
|---|---|---|---|
| 0.000 | 0.0 | 0.0 | 0.0 |
| 0.010 | −30.2 | −52.0 | −68.8 |
| 0.022 | −55.3 | −64.0 | −71.9 |
| 0.046 | −68.2 | −80.0 | −100.0 |
| 0.100 | −88.9 | −96.0 | −100.0 |

| Quetiapine (mg · kg⁻¹) | A Quet | B Quet. + 1 mg Mirt. |
|---|---|---|
| 0.0 | 0.0 | 0.0 |
| 1.0 |  | −41.4 |
| 2.2 | −35.3 | −82.8 |
| 4.6 | −67.7 | −100.0 |
| 10.0 | −97.1 | −100.0 |
| 22.0 | −100.0 |  |

What is claimed is:

1. A combination comprising mirtazapine and an antipsychotic agent.

2. A combination according to claim 1 wherein the antipsychotic agent is a typical or atypical antipsychotic agent.

3. A combination according to claim 1 wherein the antipsychotic agent is acepromazine, chlorproethazine, chlorpromazine, cyamemazine fluopromazine, methotrimeprazine, promazine, mesoridazine, pericyazine, piperacetazine, pipothiazine, sulforidazine, thioridazine, acetophenazine, carphenazine, dixyrazine, fluphenazine, perazine, perphenazine, prochlorperazine thiopropazate, thioproperazine, trifluperazine, chlorprothixene, flupenthixol, thiothixene, zuclopenthixol, benperidol, bromperidol, droperidol, fluanisone, haloperidol, melperone, moperone, pipamperone, spiperone, timiperone, trifluperidol, fluspirilene, penfluridol, pimozide, amisulpride, raclopride, remoxipride, sulpiride, sultopride, tiapride, molindone, oxypertine, clozapine, loxapine, risperidone, olanzapine, sertindole, quetiapine or ziprasidone.

4. A combination according to claim 1 wherein the antipsychotic agent is acepromazine, chlorpromethazine, chlorpromazine, cyamemazine fluopromazine, methotrimeprazine, promazine, mesoridazine, pericyazine, piperacetazine, pipothiazine, sulforidazine, thioridazine, acetophenazine, carphenazine, dixyrazine, fluphenazine, perazine, perphenazine, prochlorperazine thiopropazate, thioproperazine, trifluperazine, chlorprothixene, flupenthixol, thiothixene, zuclopenthixol, benperidol, bromperidol, droperidol, fluanisone, haloperidol, melperone, moperone, pipamperone, spiperone, timiperone, trifluperidol, fluspirilene, penfluridol, pimozide, amisulpride, raclopride, remoxipride, sulpiride, sultopride, tiapride, molindone, oxypertine, clozapine, loxapine, risperidone or olanzapine.

5. A pharmaceutical formulation comprising a combination according to claim 1 in association with one or more pharmaceutically acceptable carriers therefor.

6. A method for the treatment of a psychotic disorder in an animal, comprising administering to said animal a therapeutically effective amount of a combination according to any one of claims 1 to 4.

7. A patient pack comprising at least one of mirtazapine and an antipsychotic agent as active ingredients, and an information insert containing directions on the use of the active ingredient(s) in a therapeutic regimen using a combination comprising mirtazapine and an antipsychotic agent.

8. A process for preparing a pharmaceutical composition, comprising mixing together mirtazapine and an antipsychotic agent.

9. The process of claim 8, further comprising adding to the mixture thereby produced one or more pharmaceutically acceptable carriers.

10. A method for the treatment of a psychotic disorder in an animal, comprising administering to said animal a therapeutically effective amount of the pharmaceutical formulation according to claim 5.

* * * * *